(12) United States Patent
Naber et al.

(10) Patent No.: US 10,863,903 B2
(45) Date of Patent: Dec. 15, 2020

(54) OCULAR SYSTEM AND METHOD

(71) Applicants: John Naber, Goshen, KY (US); Doug Jackson, New Albany, IN (US); Rich Eiferman, Louisville, KY (US)

(72) Inventors: John Naber, Goshen, KY (US); Doug Jackson, New Albany, IN (US); Rich Eiferman, Louisville, KY (US)

(73) Assignee: ADVANCED OPHTHALMICS LLC, Wilmington, DE (US)

( * ) Notice: Subject to any disclaimer, the term of this patent is extended or adjusted under 35 U.S.C. 154(b) by 328 days.

(21) Appl. No.: 16/010,486

(22) Filed: Jun. 17, 2018

(65) Prior Publication Data

US 2019/0380578 A1 Dec. 19, 2019

(51) Int. Cl.
*H05K 3/30* (2006.01)
*A61B 3/16* (2006.01)
*H05K 1/03* (2006.01)
*A61F 9/007* (2006.01)
*A61B 3/00* (2006.01)

(52) U.S. Cl.
CPC .............. *A61B 3/16* (2013.01); *A61B 3/0025* (2013.01); *A61F 9/00781* (2013.01); *H05K 1/0393* (2013.01); *A61B 2562/12* (2013.01); *H05K 2201/10015* (2013.01)

(58) Field of Classification Search
USPC .................................. 29/832, 841, 846, 848
See application file for complete search history.

(56) References Cited

U.S. PATENT DOCUMENTS 9,307,901 B1 * 4/2016 Linhardt ................ A61B 3/101
9,789,655 B1 * 10/2017 Weibel .................. B29C 70/685

* cited by examiner

*Primary Examiner* — Donghai D Nguyen
(74) *Attorney, Agent, or Firm* — Chris Tanner; TannerPatent.com

(57) ABSTRACT

A system and method for remotely monitoring Inter Ocular Pressure (IOP) is disclosed. The system and method verify proper operation of glaucoma drainage, measure and potentially affect Intra-Ocular Pressure (IOP), and facilitate remote disease management of e.g. glaucoma, among other ocular diseases.

16 Claims, 15 Drawing Sheets

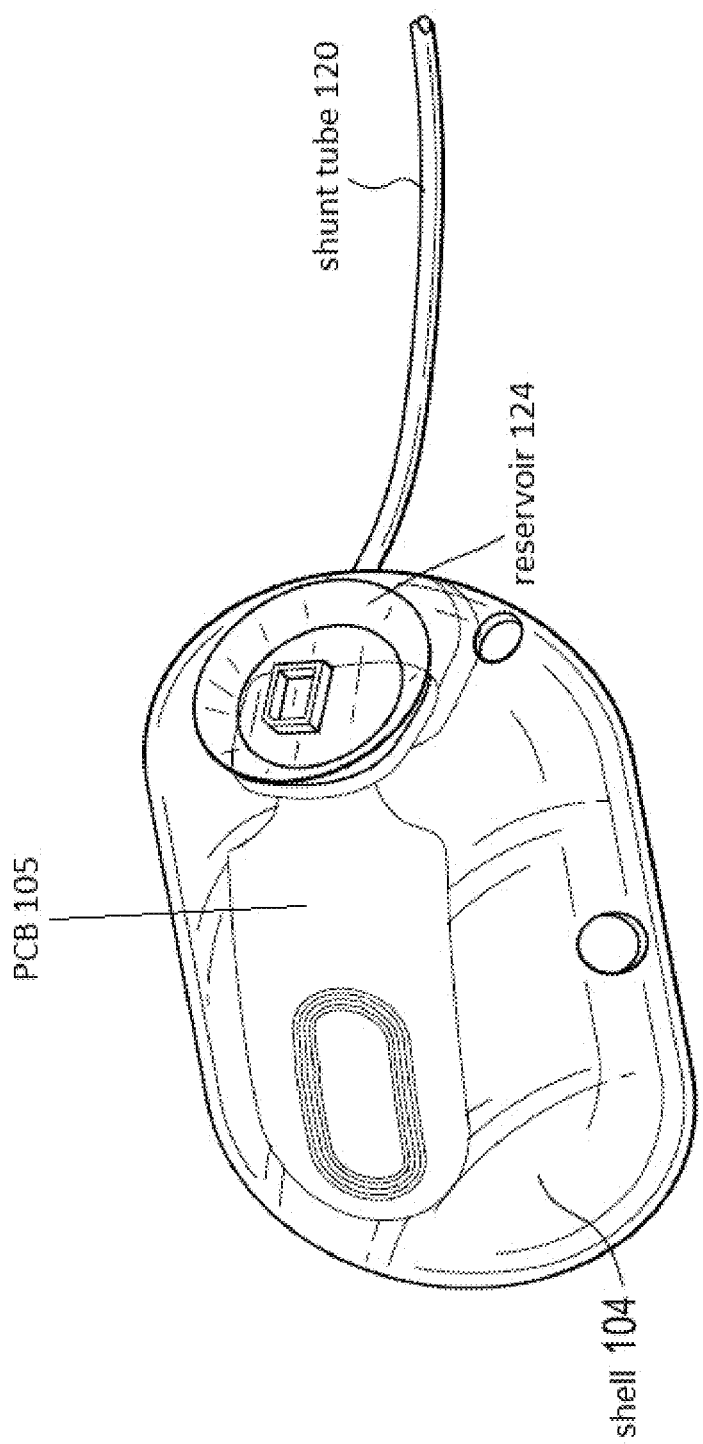
FIG. 5 (PCB 105 mounted on eye-socket-facing portion of shell 104)

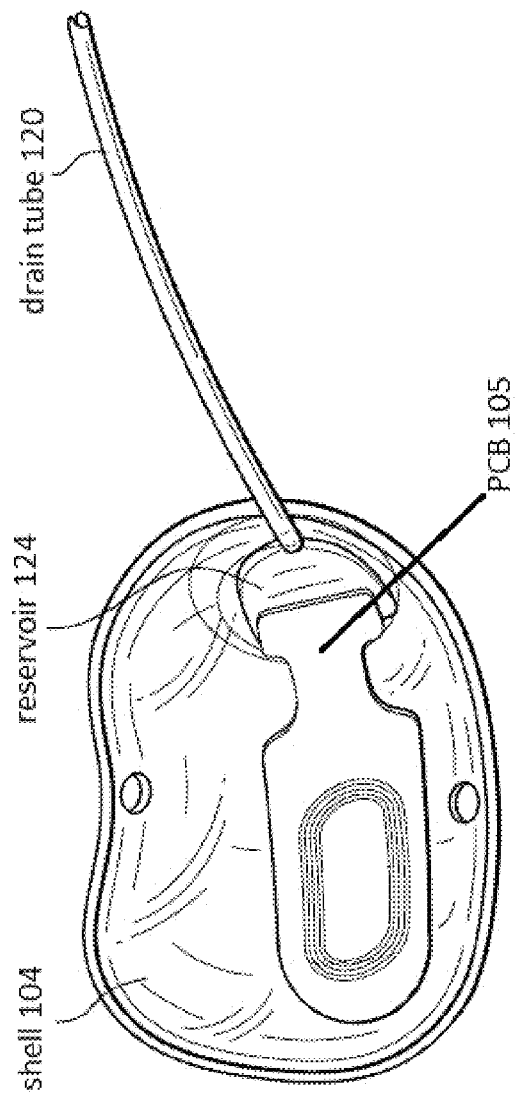
FIG. 6 (PCB 105 mounted on eyeball-facing surface of shell 104)

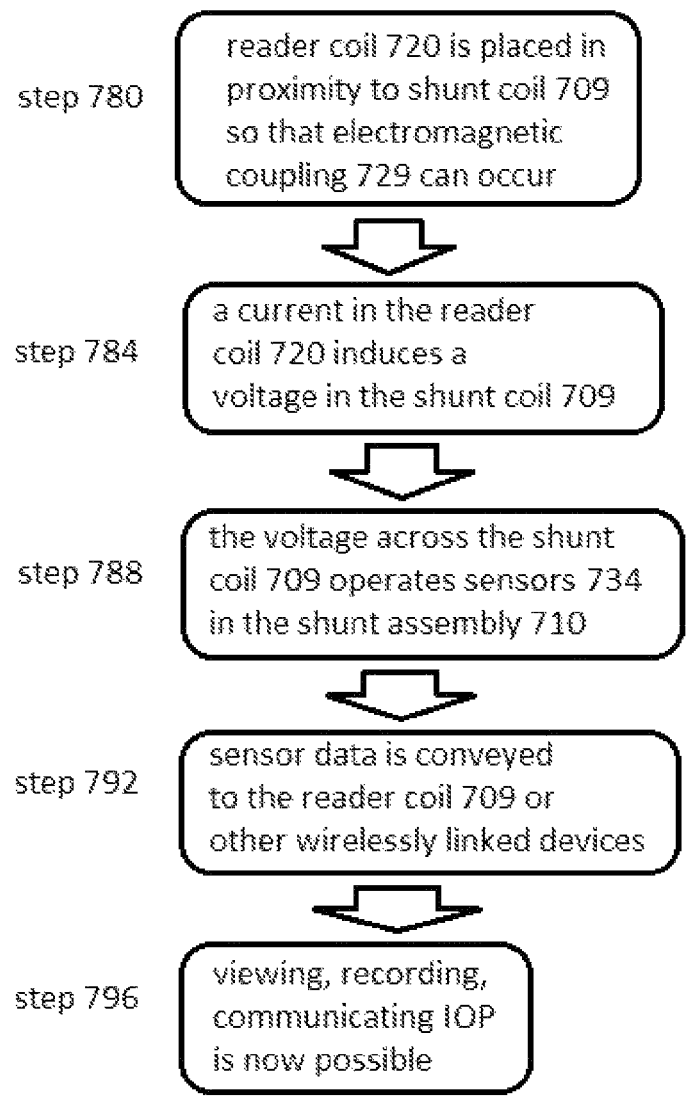
FIG. 7C (method of operation)

| index | reference (mmHg) | Pressure 1 shunt chamber (mmHg) | Pressure Anterior chamber (mmHg) | Temp shunt chamber (degC) | Temp Anterior chamber (degC) | elapsed time (s) | Shunt (mmHg) | Reference offset to zero | shunt chamber offset to zero | anterior chamber offset to zero | RFID offset to zero |
|---|---|---|---|---|---|---|---|---|---|---|---|
| 1 | 24.13362 | 627.9825 | 689.8575 | 25.03 | 22.95 | 0 | | 0 | 0 | 0 | 0 |
| 2 | 24.13362 | 627.9825 | 689.8575 | 25.05 | 22.97 | 3.127 | 704.488 | 0 | 0 | 0 | -0.286377 |
| 3 | 24.13362 | 627.9825 | 689.955 | 25.06 | 22.97 | 6.152 | 704.202 | 0 | 0 | 0.0975 | 0.0765381 |
| 4 | 25.01121 | 628.5 | 690.66 | 25.06 | 22.99 | 9.21 | 704.565 | 0.877586 | 0.5175 | 0.8025 | 0.292856 |
| 5 | 25.88879 | 629.25 | 691.3575 | 25.06 | 22.98 | 11.25 | 704.719 | 1.755172 | 1.2675 | 1.5 | 1.0929565 |
| 6 | 26.76638 | 629.955 | 692.16 | 25.07 | 22.99 | 15.381 | 705.581 | 2.622759 | 1.9725 | 2.3025 | 1.6697388 |
| 7 | 26.98578 | 630.66 | 692.8125 | 25.07 | 22.98 | 18.471 | 706.158 | 2.852759 | 2.6775 | 2.955 | 2.3391209 |
| 8 | 28.08276 | 631.3575 | 693.6075 | 25.07 | 22.99 | 21.553 | 706.847 | 3.949138 | 3.375 | 3.75 | 3.0732563 |
| 9 | 28.52155 | 632.0625 | 694.2225 | 25.08 | 23 | 24.695 | 707.563 | 4.387931 | 4.08 | 4.365 | 3.75 |
| 10 | 29.17924 | 632.67 | 694.785 | 25.08 | 23 | 27.727 | 708.238 | 5.046121 | 4.6875 | 4.9275 | 4.448643 |
| 11 | 29.83793 | 633.33 | 695.295 | 25.08 | 23 | 30.836 | 708.936 | 5.70431 | 5.3475 | 5.4375 | 5.2421365 |
| 12 | 30.93491 | 633.8475 | 695.91 | 25.08 | 23 | 33.841 | 709.73 | 6.801293 | 5.865 | 6.0525 | 5.5704346 |
| 13 | 31.37071 | 634.5975 | 696.66 | 25.08 | 22.99 | 36.924 | 710.058 | 7.240086 | 6.615 | 6.8025 | 6.5169619 |
| 14 | 32.25129 | 635.295 | 697.3125 | 25.08 | 23 | 40.538 | 711.005 | 8.117672 | 7.3125 | 7.455 | 7.2211304 |
| 15 | 32.47069 | 635.8575 | 697.875 | 25.09 | 23 | 43.665 | 711.709 | 8.337069 | 7.875 | 8.0175 | 7.7651367 |
| 16 | 33.56767 | 636.42 | 698.4825 | 25.09 | 23 | 46.671 | 712.259 | 9.434051 | 8.4375 | 8.625 | 8.2454224 |
| 17 | 33.78707 | 637.08 | 699.0975 | 25.09 | 23 | 49.723 | 712.733 | 9.653448 | 9.0975 | 9.24 | 8.8392234 |
| 18 | 34.66465 | 637.785 | 699.6075 | 25.09 | 23 | 52.81 | 713.327 | 10.53103 | 9.8025 | 9.75 | 9.472229 |
| 19 | 34.88405 | 638.295 | 700.2225 | 25.1 | 23.01 | 55.948 | 713.98 | 10.75043 | 10.3125 | 10.365 | 10.162537 |
| 20 | 35.76164 | 638.91 | 700.785 | 25.1 | 23 | 58.94 | 714.651 | 11.62802 | 10.9275 | 10.9375 | 10.667175 |
| 21 | 36.41903 | 639.42 | 701.3925 | 25.09 | 23 | 62.082 | 715.155 | 12.28621 | 11.4375 | 11.535 | 11.311805 |
| 22 | 36.85862 | 639.9825 | 701.955 | 25.09 | 23 | 65.22 | 715.801 | 12.38621 | 12 | 12.0975 | 11.862854 |
| 23 | 37.29741 | 640.545 | 702.5175 | 25.1 | 23 | 68.334 | 716.351 | 12.725 | 12.5625 | 12.66 | 12.142738 |
| 24 | 37.73621 | 641.0625 | 703.08 | 25.1 | 23 | 71.326 | 716.731 | 13.18379 | 13.08 | 13.2225 | 12.920837 |
| 25 | 38.83319 | 641.67 | 703.5975 | 25.1 | 23 | 74.376 | 717.409 | 13.60259 | 13.6875 | 13.74 | 13.460449 |
| 26 | 39.05259 | 642.2325 | 704.16 | 25.1 | 23 | 77.517 | 717.948 | 14.69957 | 14.25 | 14.3025 | 14.03864 |
| 27 | 39.49138 | 642.75 | 704.7225 | 25.1 | 23.01 | 80.55 | 718.519 | 14.91897 | 14.7675 | 14.865 | 14.645691 |
| 28 | 40.14957 | 643.2325 | 705.285 | 25.1 | 23.01 | 83.649 | 719.134 | 15.35776 | 15.24 | 15.4275 | 15.166443 |
| 29 | 41.02715 | 643.83 | 705.795 | 25.11 | 23.01 | 86.758 | 719.654 | 16.01595 | 15.8475 | 15.9375 | 15.76353 |
| 30 | 41.24655 | 644.3475 | 706.3575 | 25.11 | 23 | 89.835 | 720.691 | 17.11293 | 16.365 | 16.5 | 16.2036088 |

FIG. 8A

| index | reference (mmHg) | Pressure 1 shunt chamber (mmHg) | Pressure Anterior chamber (mmHg) | Temp shunt chamber (degC) | Temp Anterior chamber (degC) | elapsed time (s) | shunt (mmHg) | Reference offset to zero | shunt chamber offset to zero | anterior chamber offset to zero | RFID offset to zero |
|---|---|---|---|---|---|---|---|---|---|---|---|
| 31 | 41.68534 | 644.8575 | 706.83 | 25.11 | 23 | 92.937 | 721.391 | 17.55172 | 16.875 | 16.9725 | 16.923649 |
| 32 | 42.56293 | 645.42 | 707.4825 | 25.11 | 23.01 | 96.066 | 721.934 | 18.42931 | 17.4375 | 17.625 | 17.44574 |
| 33 | 42.78233 | 645.9375 | 707.91 | 25.11 | 23 | 99.091 | 722.261 | 18.64871 | 17.955 | 18.0525 | 17.772949 |
| 34 | 43.65991 | 646.5 | 708.4725 | 25.11 | 23.01 | 102.164 | 722.936 | 19.52629 | 18.5175 | 18.615 | 18.468018 |
| 35 | 44.5375 | 647.0175 | 709.08 | 25.11 | 23.01 | 105.294 | 723.498 | 20.40388 | 19.035 | 19.2225 | 19.03001 |
| 36 | 44.7969 | 647.535 | 709.5975 | 25.11 | 23.01 | 108.348 | 723.903 | 20.62328 | 19.5525 | 19.74 | 19.414856 |
| 37 | 45.63448 | 648 | 710.0625 | 25.11 | 23.01 | 111.46 | 724.492 | 21.50086 | 20.0175 | 20.205 | 20.004289 |
| 38 | 45.63448 | 648.5625 | 710.625 | 25.12 | 23 | 114.599 | 725.022 | 21.50086 | 20.58 | 20.7675 | 20.33363 |
| 39 | 46.51207 | 649.095 | 711.1425 | 25.12 | 23.01 | 117.727 | 725.809 | 22.37845 | 21.0525 | 21.285 | 21.320801 |
| 40 | 47.17028 | 649.5975 | 711.705 | 25.12 | 23.01 | 120.846 | 726.208 | 23.03604 | 21.615 | 21.8475 | 21.717773 |
| 41 | 47.60908 | 650.0625 | 712.17 | 25.12 | 23.01 | 123.966 | 726.741 | 23.47543 | 22.08 | 22.3125 | 22.252991 |
| 42 | 47.82845 | 650.58 | 712.7325 | 25.12 | 23.01 | 126.978 | 727.419 | 23.68483 | 22.5975 | 22.875 | 22.931213 |
| 43 | 48.70603 | 651.045 | 713.25 | 25.12 | 23.01 | 130.046 | 727.786 | 24.57241 | 23.0625 | 23.3925 | 23.297791 |
| 44 | 48.92543 | 651.6075 | 713.7225 | 25.13 | 23.01 | 133.159 | 728.111 | 24.79181 | 23.625 | 23.865 | 23.712778 |
| 45 | 49.14483 | 652.035 | 714.2325 | 25.13 | 23.01 | 136.269 | 728.674 | 25.01121 | 24.0525 | 24.375 | 24.186218 |
| 46 | 49.80302 | 652.5975 | 714.8925 | 25.12 | 23.01 | 139.374 | 729.217 | 25.6684 | 24.615 | 25.035 | 24.729309 |
| 47 | 50.46121 | 653.16 | 715.41 | 25.13 | 23.02 | 142.33 | 729.832 | 26.32759 | 25.1775 | 25.5525 | 25.343628 |
| 48 | 50.9 | 653.535 | 715.875 | 25.13 | 23.01 | 145.67 | 730.362 | 26.76638 | 25.5525 | 26.0175 | 25.874451 |
| 49 | 51.77758 | 654.045 | 716.3475 | 25.13 | 23.01 | 148.701 | 730.696 | 27.64386 | 26.0625 | 26.49 | 26.210449 |
| 50 | 51.99648 | 654.5375 | 716.8575 | 25.13 | 23.01 | 151.824 | 731.294 | 27.86536 | 26.535 | 27 | 26.805542 |
| 51 | 52.43577 | 655.08 | 717.375 | 25.13 | 23.01 | 154.924 | 731.719 | 28.30215 | 27.0975 | 27.5175 | 27.230713 |
| 52 | 52.87457 | 655.5 | 717.8475 | 25.14 | 23.01 | 158.039 | 732.256 | 28.74095 | 27.5175 | 27.99 | 27.769592 |
| 53 | 53.75215 | 655.9725 | 718.3575 | 25.14 | 23.02 | 161.086 | 732.721 | 29.61853 | 27.99 | 28.5 | 28.232666 |
| 54 | 54.19295 | 656.4825 | 718.875 | 25.14 | 23.02 | 164.178 | 733.403 | 30.05733 | 28.5 | 29.0175 | 28.915283 |
| 55 | 54.41034 | 656.955 | 719.25 | 25.14 | 23.02 | 167.254 | 733.761 | 30.27073 | 28.9725 | 29.3925 | 29.272438 |
| 56 | 55.06853 | 657.42 | 719.8125 | 25.14 | 23.01 | 170.293 | 734.249 | 30.93491 | 29.4375 | 29.955 | 29.760864 |
| 57 | 55.50733 | 657.9975 | 720.2325 | 25.14 | 23.01 | 173.38 | 734.59 | 31.37371 | 29.955 | 30.375 | 30.10199 |
| 58 | 55.94612 | 658.5 | 720.75 | 25.14 | 23.01 | 176.509 | 735.282 | 31.8125 | 30.5175 | 30.8925 | 30.794861 |
| 59 | 56.38491 | 658.92 | 721.17 | 25.14 | 23.01 | 179.613 | 735.815 | 32.25129 | 30.9375 | 31.3125 | 31.285599 |
| 60 | 56.82371 | 659.3475 | 721.785 | 25.15 | 23.02 | 182.702 | 736.111 | 32.69009 | 31.365 | 31.9275 | 31.722473 |

FIG. 8B

| index | reference (mmHg) | Pressure 1 shunt chamber (mmHg) | Pressure Anterior chamber (mmHg) | Temp shunt chamber (degC) | Temp Anterior chamber (degC) | elapsed time (s) | Shunt (mmHg) | Reference offset to zero | shunt chamber offset to zero | anterior chamber offset to zero | RFID offset to zero |
|---|---|---|---|---|---|---|---|---|---|---|---|
| 61 | 57.92089 | 659.91 | 722.25 | 25.15 | 23.02 | 185.747 | 736.782 | 33.78707 | 31.9275 | 32.3925 | 32.293945 |
| 62 | 57.92089 | 660.375 | 722.7675 | 25.15 | 23.02 | 189.806 | 737.086 | 33.78707 | 32.3925 | 32.91 | 32.590267 |
| 63 | 58.78827 | 660.8475 | 723.2325 | 25.15 | 23.01 | 191.853 | 737.586 | 34.66465 | 32.865 | 33.375 | 33.097778 |
| 64 | 59.23707 | 661.3575 | 723.75 | 25.16 | 23.01 | 194.936 | 738.007 | 35.10345 | 33.375 | 33.8925 | 33.516855 |
| 65 | 59.45648 | 661.83 | 724.2225 | 25.16 | 23.02 | 196.047 | 738.603 | 35.32284 | 33.8475 | 34.365 | 34.114563 |
| 66 | 60.33405 | 662.3475 | 724.7325 | 25.15 | 23.02 | 203.179 | 739.054 | 36.20043 | 34.365 | 34.875 | 34.565552 |
| 67 | 60.53345 | 662.8125 | 725.205 | 25.15 | 23.02 | 204.287 | 739.757 | 36.41983 | 34.83 | 35.3475 | 35.268494 |
| 68 | 61.43109 | 663.285 | 725.7225 | 25.15 | 23.02 | 207.377 | 740.151 | 37.29741 | 35.3025 | 35.865 | 35.663269 |
| 69 | 61.86983 | 663.795 | 726.2325 | 25.15 | 23.02 | 210.503 | 740.763 | 37.73621 | 35.8125 | 36.375 | 36.274475 |
| 70 | 62.30862 | 664.1675 | 726.705 | 25.16 | 23.02 | 213.537 | 741.061 | 38.175 | 36.185 | 36.8475 | 36.573303 |
| 71 | 62.52802 | 664.7325 | 727.17 | 25.16 | 23.01 | 216.614 | 741.416 | 38.3944 | 36.75 | 37.3125 | 36.928345 |
| 72 | 63.4056 | 665.295 | 727.6875 | 25.16 | 23.03 | 219.694 | 742.147 | 39.27198 | 37.3125 | 37.83 | 37.658936 |
| 73 | 63.625 | 665.7225 | 728.16 | 25.17 | 23.02 | 222.674 | 742.694 | 39.49138 | 37.74 | 38.3025 | 38.208421 |
| 74 | 64.06379 | 666.285 | 728.67 | 25.16 | 23.03 | 225.749 | 743.141 | 39.93017 | 38.3025 | 38.8125 | 38.652649 |
| 75 | 64.72198 | 666.75 | 729.1875 | 25.16 | 23.02 | 228.856 | 743.662 | 40.58836 | 38.7675 | 39.23 | 39.173584 |
| 76 | 65.16077 | 667.17 | 729.75 | 25.16 | 23.03 | 231.964 | 744.217 | 41.02715 | 39.1875 | 39.6925 | 39.729809 |
| 77 | 65.59957 | 667.7325 | 730.2225 | 25.17 | 23.03 | 235.006 | 744.568 | 41.46595 | 39.75 | 40.365 | 40.079773 |
| 78 | 66.47715 | 668.205 | 730.7325 | 25.17 | 23.02 | 238.173 | 745.112 | 42.34353 | 40.2225 | 40.875 | 40.623779 |
| 79 | 66.91595 | 668.625 | 731.16 | 25.17 | 23.02 | 241.281 | 745.564 | 42.78233 | 40.6425 | 41.3025 | 41.0755 |
| 80 | 67.57414 | 669.1425 | 731.67 | 25.18 | 23.03 | 244.362 | 746.216 | 43.44052 | 41.16 | 41.8125 | 41.727905 |
| 81 | 67.79353 | 669.66 | 732.2325 | 25.17 | 23.02 | 247.499 | 746.601 | 43.65991 | 41.6775 | 42.375 | 42.11261 |
| 82 | 68.23233 | 669.75 | 732.66 | 25.17 | 23.02 | 250.613 | 747.197 | 44.09871 | 42.0525 | 42.8025 | 42.708801 |
| 83 | 69.10991 | 670.6425 | 733.17 | 25.17 | 23.02 | 253.665 | 747.347 | 44.97629 | 42.66 | 43.3125 | 43.058533 |
| 84 | 69.10991 | 671.16 | 733.7325 | 25.17 | 23.02 | 256.673 | 747.797 | 44.97629 | 43.1775 | 43.875 | 43.308655 |
| 85 | 69.9875 | 671.58 | 734.16 | 25.18 | 23.03 | 259.741 | 748.624 | 45.85368 | 43.5975 | 44.3025 | 44.136108 |
| 86 | 70.64569 | 672.045 | 734.7675 | 25.18 | 23.03 | 262.783 | 749.191 | 46.51207 | 44.06 | 44.91 | 44.703003 |
| 87 | 70.86508 | 672.5625 | 735.2325 | 25.17 | 23.03 | 265.932 | 749.494 | 46.73146 | 44.58 | 45.375 | 45.005676 |
| 88 | 71.30388 | 673.08 | 735.705 | 25.18 | 23.03 | 269.039 | 750.024 | 47.17026 | 45.0975 | 45.8475 | 45.535859 |

FIG. 8C

OCULAR SYSTEM AND METHOD

BACKGROUND OF THE INVENTION

For persons suffering from various eye diseases e.g. glaucoma, it is useful to measure and adjust their IntraOcular Pressure (IOP). However, mechanisms for measuring IOP have various limitations. There is a definite relationship between the level of IOP and the likelihood that the eye would lose sight; the higher the IOP, the greater the chance that the eye would become blind. Therefore, IOP remained the primary focus in the diagnosis and treatment of glaucoma for many years.

The intraocular pressure (IOP) of the eye is determined by the balance between the amount of aqueous humor—that the eye makes and the ease with which it leaves the eye. One way to measure IPO is the Goldmann equation, which states:

$$Po=(F/C)+Pv \ldots$$

where Po is the IOP in millimeters of mercury (mmHg), F is the rate of aqueous formation, C is the facility of outflow, and Pv is the episcleral venous pressure.

The relationship between IOP and glaucoma continues to be explored further, but at present appears that IOP remains the only significantly modifiable risk factor in the treatment of glaucoma at present. Treatment is initiated in eyes that have developed glaucomatous optic nerve damage and/or visual field loss, or in eyes at significant risk for developing glaucoma. IOP is then lowered to a 'target level' determined by many factors including baseline level of IOP, extent of damage, rate of prior change, risk factors, life expectancy, medical history, and family history. The target IOP is constantly reevaluated to ensure stability of the optic nerve and visual field and to ultimately preserve patient's visual function. One way to evaluate IOP is using tonometry, of which there are numerous varieties.

The Goldmann applanation tonometer measures the force necessary to flatten an area of the cornea of 3.06 mm diameter. At this diameter, the resistance of the cornea to flattening is counterbalanced by the capillary attraction of the tear film meniscus for the tonometer head. The IOP (in mm Hg) equals the flattening force (in grams) multiplied by 10. Fluorescein dye is placed in the patient's eye to highlight the tear film. A split-image prism is used such that the image of the tear meniscus is divided into a superior and inferior arc. The intraocular pressure is taken when these arcs are aligned such that their inner margins just touch.

Applanation tonometry measurements are affected by the central corneal thickness (CCT). When Goldmann designed his tonometer, he estimated an average corneal thickness of 520 microns to cancel the opposing forces of surface tension and corneal rigidity to allow indentation. It is now known that a wide variation exists in corneal thickness among individuals. As such, thicker CCT may give an artificially high IOP measurement, whereas thinner CCT can give an artificially low reading.

Other errors that may affect the accuracy of readings from a Goldmann tonometer include excessive or insufficient fluorescein in the tear film, high astigmatism, irregular or scarred cornea, pressure from a finger on the eyelid while taking the measurement, and breath holding and Valsalva maneuver by the patient during measurement.

At present, measuring IOP is achieved largely by a handheld tonometer operated by a human. Specifically, tonometer measurements are typically made by medical staff at a clinic, at various time-intervals. These measurements are not automated, but instead require a human perform the measurement task, which is delicate, requires direct contact with the eye, and requires careful use in order to avoid both infection and incorrect readings. As such, the measurements cannot be self-administered.

Some conventional drainage devices may include a sensor, but this refers merely to pressure-regulation devices where that sensor communicates only with a drainage device itself, and does not communicate any information externally. Consequently, environments using such conventional drainage devices still require conventional IOP measurements be taken, with all of the risks and expense associated therewith.

Further, various of the existing IOP measurement devices may require the patient to wear a special contact lens, which is too challenging for much of the glaucoma population. Meanwhile, implanted IOP sensors exist, but are implanted in an anterior chamber of the eye, requiring a complex surgical procedure.

Consequently, a more effective mechanism for managing and adjusting IOP is desired.

BRIEF DESCRIPTION OF THE DRAWINGS

FIG. 5 shows an example of the circuit board positioned on an outer (facing away from the eyeball) surface of the shell of the drainage device;

FIG. 6 shows another example of the circuit board positioned on an inner (eye-ball facing) surface of the shell 104 of the drainage device;

FIG. 7C shows a method of operating that embodiment;

FIGS. 8A, 8B, and 8C show data accumulated from running 88 separate pressure tests, over time;

SUMMARY OF THE INVENTION

At a minimum, the embodiments described herein can do the following:

verify proper operation of glaucoma drainage;

measure and potentially affect Intra-Ocular Pressure (IOP); and/or facilitate remote disease management of e.g. glaucoma, among other ocular diseases.

DETAILED DESCRIPTION OF THE PREFERRED EMBODIMENTS

Figure 1:
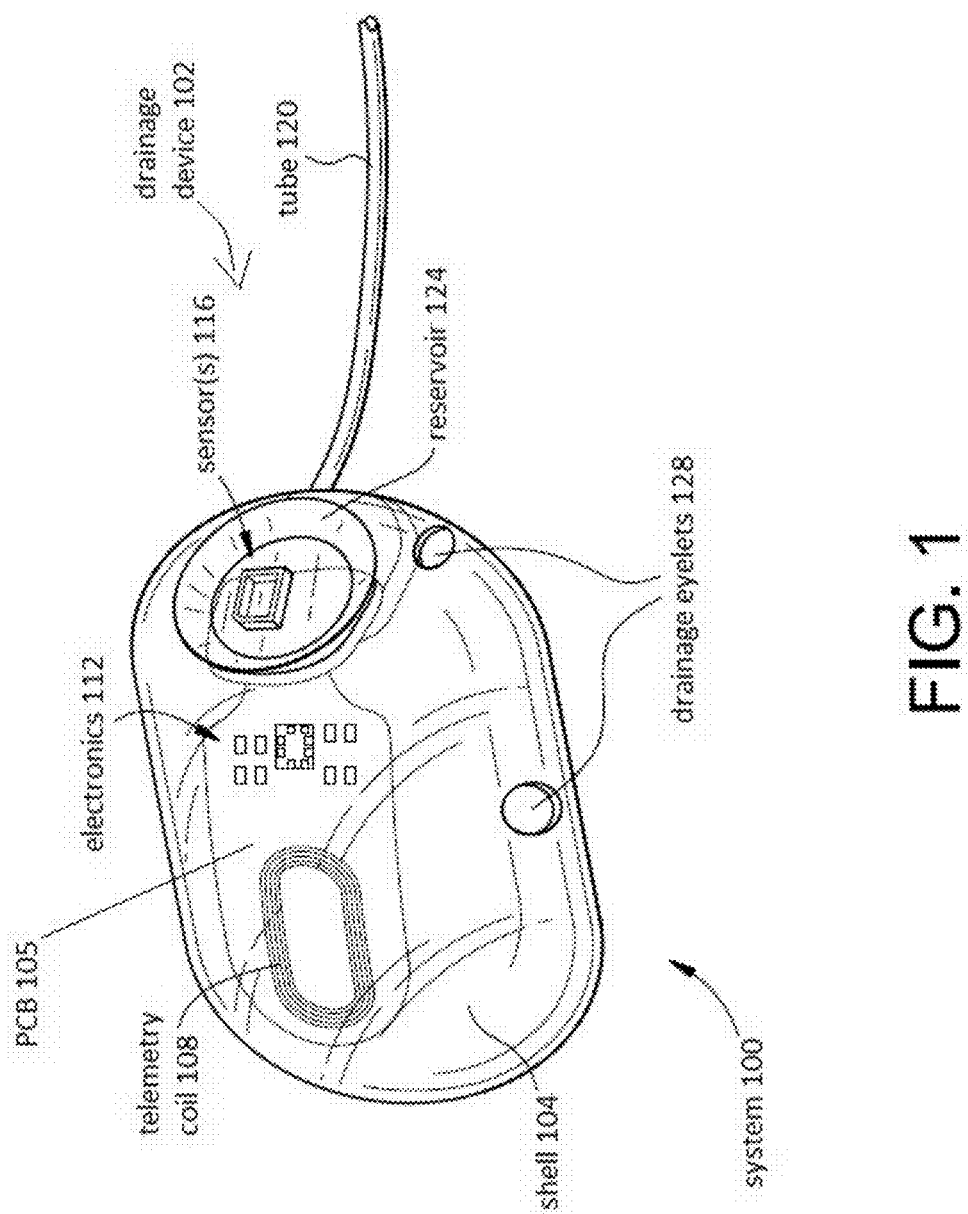
FIG. 1 shows a first embodiment of a system comprising one or more electronic sensor(s) and wireless telemetry integrated within a drainage device.

FIG. 1 shows a first embodiment of a system 100 comprising one or more electronic sensor(s) 116 and wireless telemetry 108 integrated within a drainage device 102. Within the medical device industry, such a drainage device is sometimes referred to as a shunt, and the tube 120 is sometimes referred to as a shunt tube 120 or drain tube 120. An arrangement 112 of low-power electronics converts one or more output(s) from the one or more sensor(s) 116 into a signal that can be wirelessly conveyed to a reader 404 (shown in more detail in FIG. 4) through the wireless telemetry 108. The reader should be located in near proximity of the drainage device 102. In various embodiments, the reader 404 has the added convenience of also providing power to the drainage device 102 so that no batteries are required for the system 100.

Figure 3:
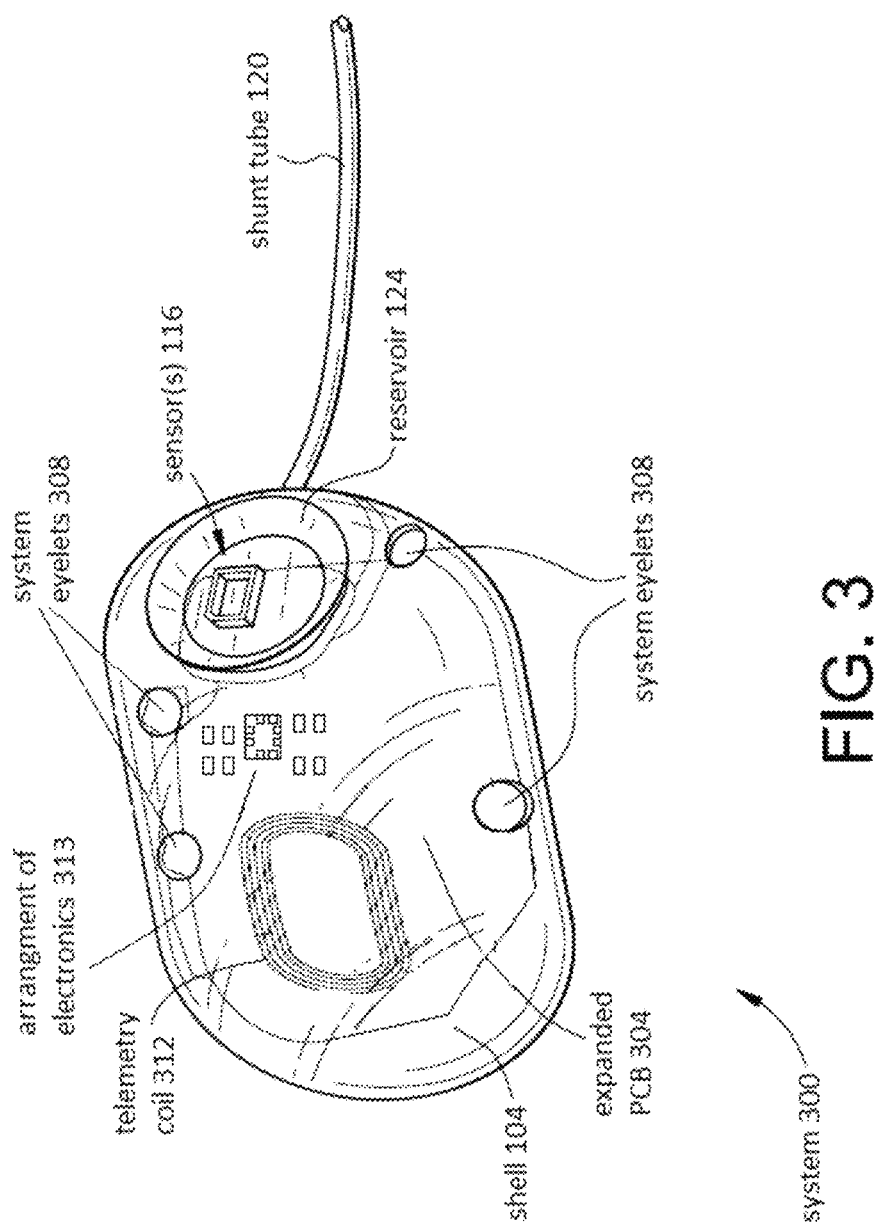
FIG. 3 shows an alternate embodiment system, which is a variation of the first embodiment.

Within FIGS. 1, 3, 5, and 6, the shell 104 upon which various features are mounted, is shown as transparent, but the shell 104 could also be opaque. Further, the shell 104 has two main surfaces/sides. The shell 104 is built\contoured to conform to the shape of a human eyeball, and thus the shell 104 always has an eyeball-facing (interior) surface, as well as an eye-socket-facing (exterior) surface. Within the embodiments disclosed herein, the PCB 105/308 can be located either in the eyeball-facing (interior) surface, or the eye-socket-facing (exterior) surface of the shell 104. Specifically, FIGS. 1, 3, and 6 show the PCB 105/308 mounted on the eyeball-facing (interior) surface of the shell 104. Meanwhile, FIG. 5 shows the PCB 105 mounted on the eye-socket-facing (exterior) surface of the shell 104.

Figure 2A:
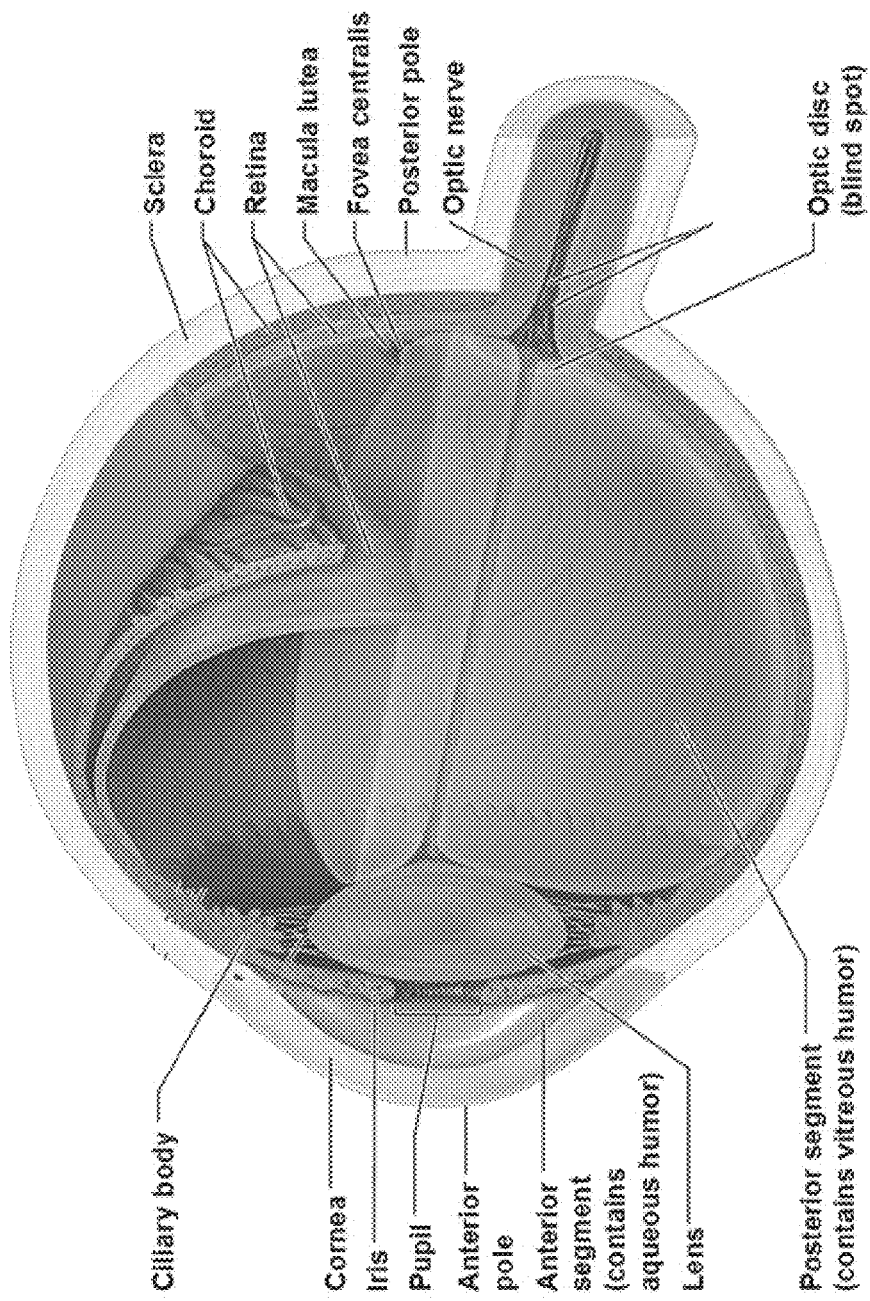
FIG. 2A shows an example installation of the system.
Figure 2B:
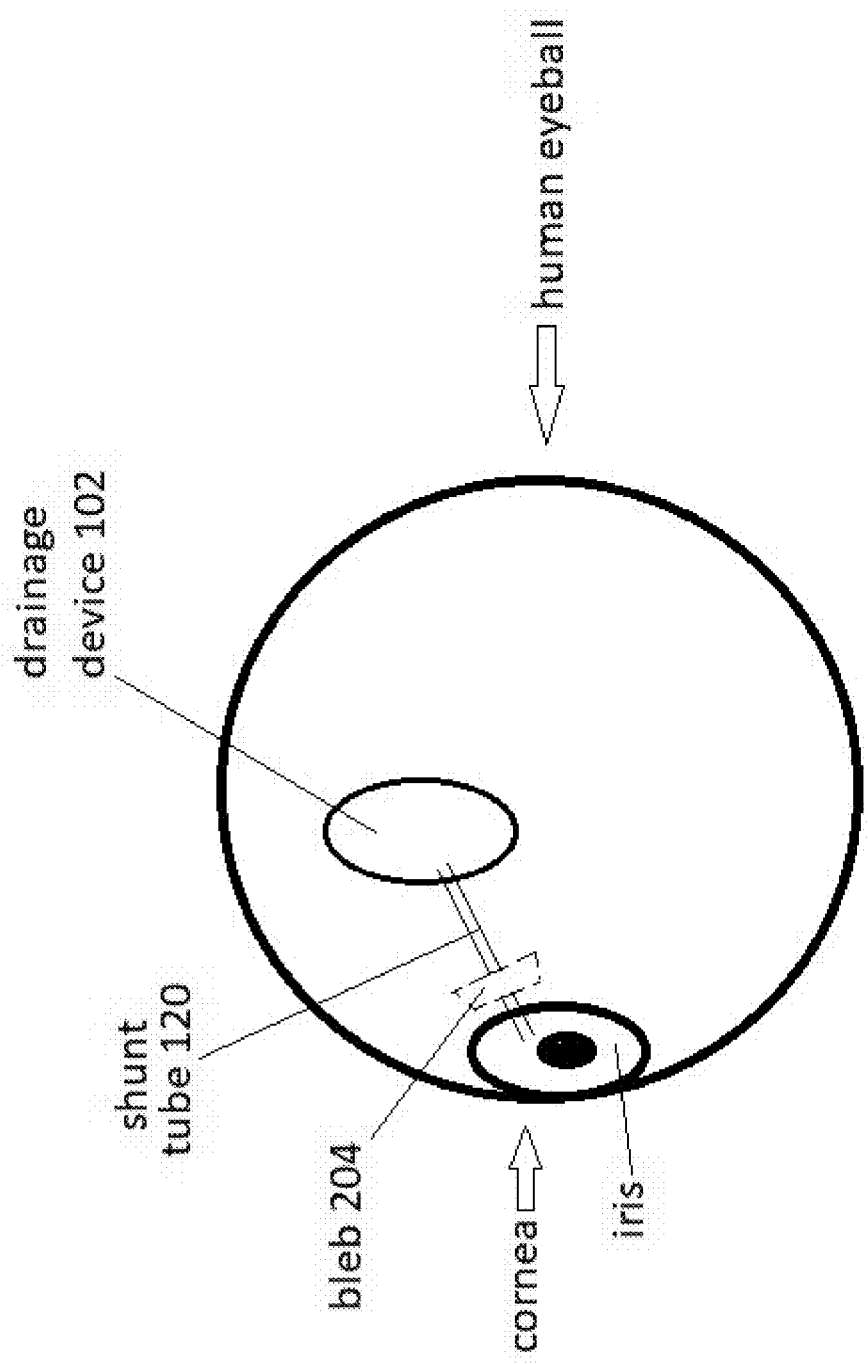
FIG. 2B (Prior Art) shows a diagram of a human eye, and in particular, the location of a sclera.

FIG. 2B shows an example installation of an embodiment of the system 100. One portion of 2B that is important is the bleb 204. The bleb 204 forms around the tube 120 after surgery, partly for the purpose of helping to prevent the sensor(s) 116 from moving out of the reservoir 124.

FIG. 2A (Prior Art) shows a diagram of a human eye, and in particular, the location of a sclera. An understanding of the location of the sclera is important because at least three configurations of the sensor 116 within the system 100 are possible. These three configurations are neither shown nor suggested by FIG. 2A, instead FIG. 2A is used merely to show location of a typical sclera:

1) the sensor(s) 116 are placed within the reservoir 124 providing data to indicate proper function of the drain tube 120 and reservoir 124;
2) the sensor(s) 116 are placed outside the reservoir 124 and against the sclera (see FIG. 2B), providing a relative indication of intraocular pressure; or
3) the arrangements of 1) and 2) are combined.

The arrangement 112 of low-power electronics can be, for example, constructed on a flexible thin film substrate and then adhered to the surfaces of the drainage device 102. The data from the drainage device 102 can include IOP pressure, strain, temperature, identifiers, or other properties of the liquid of tissue in contact with the sensor(s) 116. To achieve all this, the types of sensor(s) 116 may include, but are not limited to: pressure, strain, IR, temperature, pH, glucose, redox, ultrasonic, or radius of curvature. The composition of the telemetry coil 108 can be, but is not limited to, inductively coupled, backscatter, far field EM, or a combination of these.

Further, regarding the wireless telemetry 108, there are some variations or possible alternative chip-implementations. First, it is possible to have a separate power source and telemetry system. For example, the inductive power section could be used to power a conventional transceiver (e.g. BlueTooth®) located on the drainage device 102. This would allow a smart phone to directly acquire the data from the system 100. Alternatively, a BlueTooth® transceiver could be added to the reader 404 and allow data and control of the system 100 from a mobile device.

Advantages and Clarifications

The system 100 does not require additional surgery to install, but instead merely piggybacks on existing surgical processes already in use and already proven successful. As such, the system 100 provides a new generation of IOP systems, where no change in the surgical installation process of the drainage device 102 is required.

The system 100 has various advantages over existing sensor devices located in an anterior chamber of the eye. A first advantage is that the system 100 is extra-ocular, and thus can either be integrated into a pre-existing already-FDA-approved drainage device 102, or be manufactured as a stand-alone completely integrated embodiment. Being integrated with a pre-existing already-FDA-approved drainage device could be advantageous in terms of a benefit from a more streamlined FDA approval path. Next, in either embodiment, the relatively large area of the shell 104 provides more space for sensor and circuit integration than with a (conventional) anterior approach. Further, the system 100 is more easily removable.

The system 100 is more removable than an anterior placed device because the installation procedure is less invasive from a surgical prospective. The system 100 is attached by sutures and then interfaces to the interior of the eye by the removable tube 120. Meanwhile, an anterior placed device would require a corneal incision to install or remove the device and sutures to close. If such an anterior place device was integrated with a corrective lens, that entire lens assembly would need to be removed and replaced. This would essentially be a cataract replacement procedure for each installation and removal of a conventional IOP system, which would be extremely impractical.

In an embodiment, the system 100 can also be corrective, and can assist in actively lowering IOP, and thus beyond only measuring IOP. Meanwhile, conventional devices that may lower IOP (not always successful) require risky surgery.

Variations to First Embodiment

FIG. 3 shows an alternate embodiment system 300, which is a variation of the first embodiment system 100. While it is clear that the system 300 shown in FIG. 3 clearly borrows from the system 100 in FIG. 1, it is also clear that some differences exist, so that re-numbering within this disclosure will be necessary. It is also important to note that various systems can be constructed from this disclosure, so that example systems 100, 300, and 700 are merely for example and should not be considered limiting. Specifically, some portions of e.g. systems 100, 300, and 700 might be combinable, while other portions may not be. Again, the layout and arrangement shown in this disclosure and Figures should be considered usable for explanation and enablement only, but should not be considered as limiting exclusively thereto. Nor should systems 100, 300, or 700 be considered mutually exclusive to each other.

Moving back to FIG. 3, the system 300 has an expanded flexible printed circuit board (PCB) 304, and also has eyelets 308. The expanded flexible PCB 304 enables a larger telemetry coil 312, which in turn gives better operating range, better distance and more reliability of signal, for the system 300. Meanwhile, the expanded flexible PCB 304 of the present invention also permits installation of more eyelets 308, which in an embodiment can line up with eyelets on a pre-existing drainage device. Such a line up facilitates easy attachment of the system 300, and minimizes sutures for the patient.

Next, within the system 300 of FIG. 3, the arrangement 313 of low-power electronics can be constructed on a flexible thin film substrate and then either adhered to or integrated within the drainage device 102 (not shown in FIG. 3). In the system 300, the data sent by the telemetry coil 108 can include but is not limited to pressure, strain, IR, temperature, pH, glucose, Redox, ultrasound, or changes to radius of curvature.

The use of flexible PCB 304 allows for bending the sensor(s) 116 at an acute angle into the reservoir for location on top of the shell 104 of the drainage device 102. A standard rigid PCB in incapable of making this bend into the reservoir 124. Also, there is no requirement to make a hole in the reservoir 124 as is the case when locating the sensing system on the bottom of the shell 104. As stated earlier, the bleb 204 (FIG. 2) that forms around the tube 120 after surgery will help to keep the sensor(s) 116 from moving out of the reservoir 124. The system 300 can be encapsulated in a biocompatible polymer like NuSil® that can be glued into place with a medical grade adhesive.

The use of flexible PCB 304 can also be configured to attach directly to existing commercially available drainage devices. This makes it possible to easily attach the systems 100\300 to an existing drainage device by minimizing the thickness and rigidity commonly associated with a conventional standard PCB process. The use of flexible PCB 304 allows for the making the one or more sensor(s) 116 conform to the additional size available on the shell 104. This advantage is best shown in FIG. 3, where the system 100\300 will give better range performance at least due to the larger size of the telemetry coil 344. It will also be helpful to align the device eyelets 128 with the system eyelets 308 contained within the flexible PCB 304. Matching up the system eyelets 308 with the device eyelets 128 avoids needing additional sutures applied to the flexible PCB 304 during installation/surgery.

Various compositions for the flexible PCB 304 are contemplated, and chosen partly on their ability to cling/adhere especially well to the shell 104. In other words, chose to conform especially well to the contours of the shell 104. This accounts for the fact that during manufacturing, each shell 104 might be slightly different in contour, even if only by a few micrometers here or there.

It is important to note that the embodiments herein have provision for re-casting of the original shell 104, including (where appropriate) making use of information about a specific patient. Specifically, factors for bendability of the shell 104 after purchase but prior to installation, where these factors are based on the specific contours of a particular patient's eyeball. One way to obtain this information is through orb-scans, but other ways exist also.

Next, most flexible substrates are polyimide polymer based. To obtain the necessary flexibility referred to herein, the thinner the better. However, very thin substrates are difficult to handle during manufacturing. Further, conductive traces need to be thick enough to obtain electrical performance. The embodiments herein achieve a balance between these factors.

Figure 4:
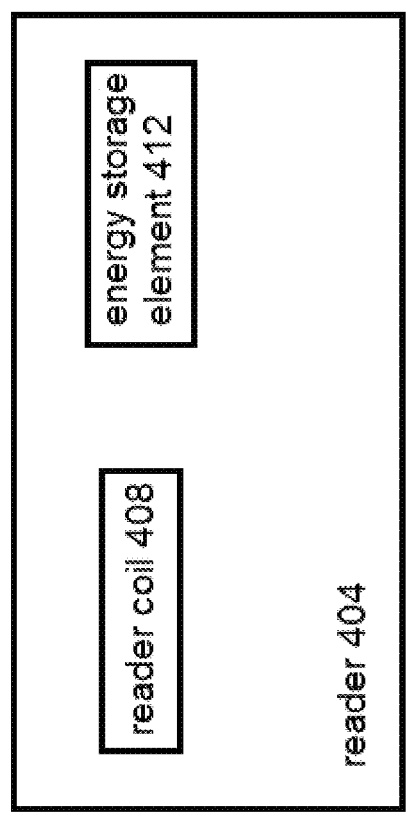
FIG. 4 shows an example of a reader.

Next, as shown in FIG. 4, the reader 404 may be a standalone device, eyeglass-integrated, medication-dispenser integrated, or could be an add-on to a mobile device. Further, partly due to the improved real-estate accorded by the expanded PCB 304, the reader 404 can include communication and network-access features including BlueTooth®, SMS, WiFi, cellular radio, as well as other communication mechanisms. The reader 404 may also include features to optimize and track eye-conditions related to glaucoma or other ocular disease that would be helpful to monitor.

The system 100 can be, for example, powered by an energy storage element 412 located within the reader 404 placed nearby, e.g. on the patient's skin adjacent to the eye socket, or perhaps attached to eyeglass frames. As such, some maintenance and observation by the patient may be helpful to successful usage of the system 100.

The reader 404 may be a standalone device or an add-on to a mobile device. The reader 404 may include features for network access including BlueTooth®, SMS, WiFi, cellular radio, and may also include features to optimize and track treatment for glaucoma or other eye disease, or conditions that a patient suffering from glaucoma or other eye disease may wish to monitor. An energy storage element 412 such as a super capacitor may be used to store the power needed to drive the system 100. The energy storage element 412 may be wirelessly rechargeable. Data could be extracted and transmitted using the reader 404.

FIG. 5 shows an example of the flexible PCB 304 positioned on an outer (facing away from the eyeball) surface of the shell 104 of the drainage device 102. Meanwhile, FIG. 6 shows another example of the flexible PCB 304 positioned on an inner (eye-ball facing) surface of the shell 104 of the drainage device 102. In other words, FIGS. 5 and 6 show the flexible PCB 304 in detail as enabling the addition of the system 100\300 to existing drainage device 102 on both the top and bottom of the shell 104. With standard rigid PCB technology, such an arrangement is not possible because rigid PCBs cannot conform to the radius of the eyeball. In FIG. 6, the flexible PCB 304 would touch the sclera (FIG. 2A).

The use of flexible PCB 304 allows for bending the sensor(s) 116 along a curved radius for mounting the sensing system on the bottom of the shell 104. A standard rigid PCB in incapable of making a curved bend along the tube 120 of the drainage device 102 that is flexible enough to follow the eye-curvature of the person wearing the system 100/300, as eye-curvature can vary considerably. Accordingly, within the embodiment shown in FIG. 6, the drainage device 102 is turned upside down to better see how the curved radius of the flexible PCB 304 follows the contour of the shell 104. This requires making a hole in the bottom of the reservoir 124. This can be done using e.g. a pinpoint heat source such as a laser, and then re-sealing of the hole using silicone, glue or other methods.

FIGS. 7A-7D describe various features of yet another embodiment, a system 700. As stated earlier, various systems can be constructed from this disclosure, so that example systems 100, 300, and 700 are shown merely for example and should not be considered limiting. Specifically, some portions of e.g. systems 100, 300, and 700 might be combinable, while other portions may not be. Again, the layout and arrangement shown in this disclosure and Figures should be considered usable for explanation and enablement only, but should not be considered as limiting exclusively thereto.

Figure 7A:
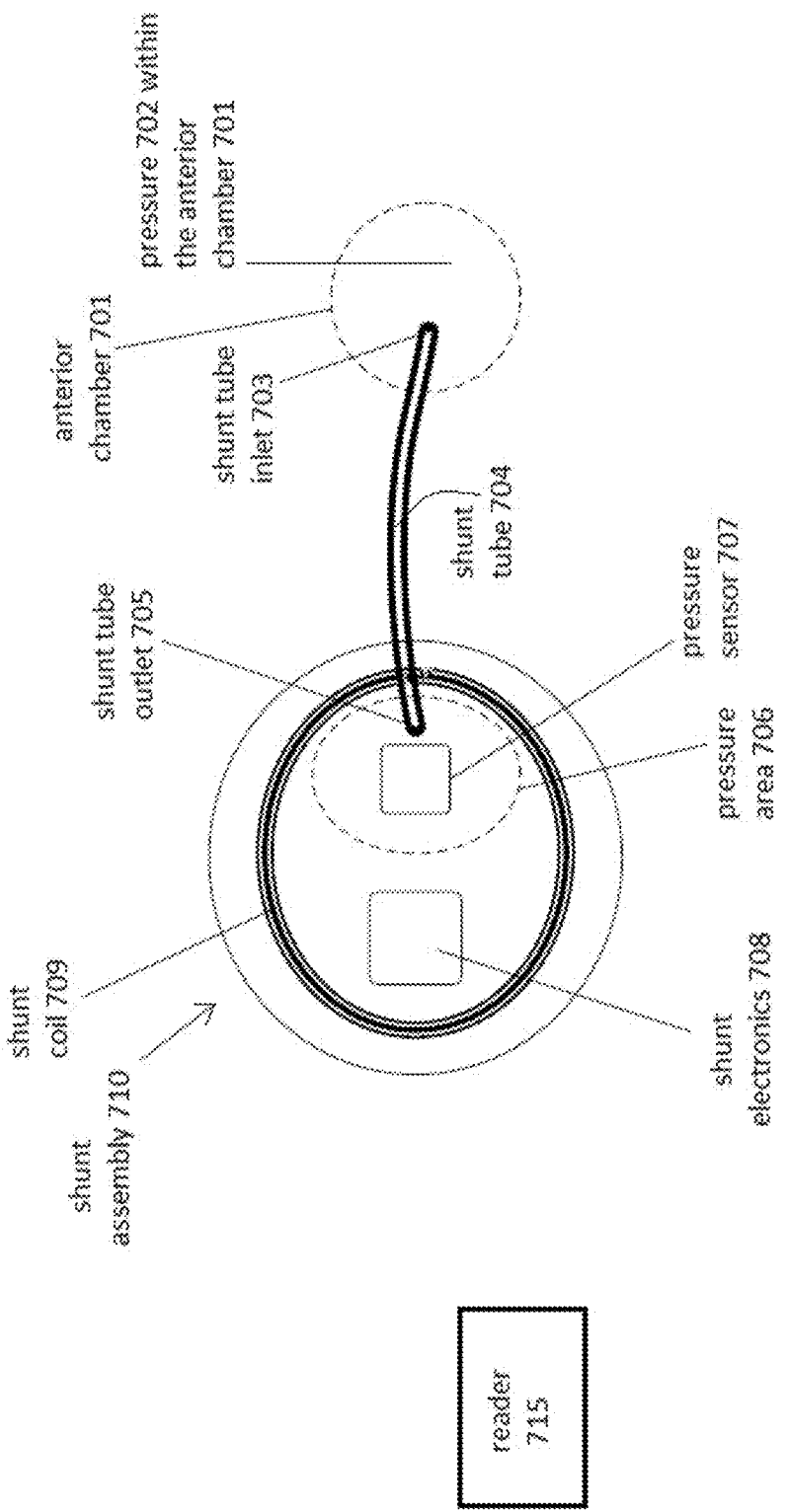
FIGS. 7A, 7B, and 7D show an additional embodiment.

FIG. 7A shows a system 700 comprising an anterior chamber 701, pressure (IOP) 702, within the anterior chamber 701 (pressure (IOP) not being a visible element, but the lead line and element number 702 merely to show an approximate area), a shunt tube inlet 703, a shunt assembly 710 comprising a shunt tube 704, shunt tube outlet 705, pressure area 706, pressure sensor 707, shunt electronics 708 (also shown in more detail in FIG. 7D), and a shunt coil 709. FIG. 7A also shows a reader 715.

Figure 7B:
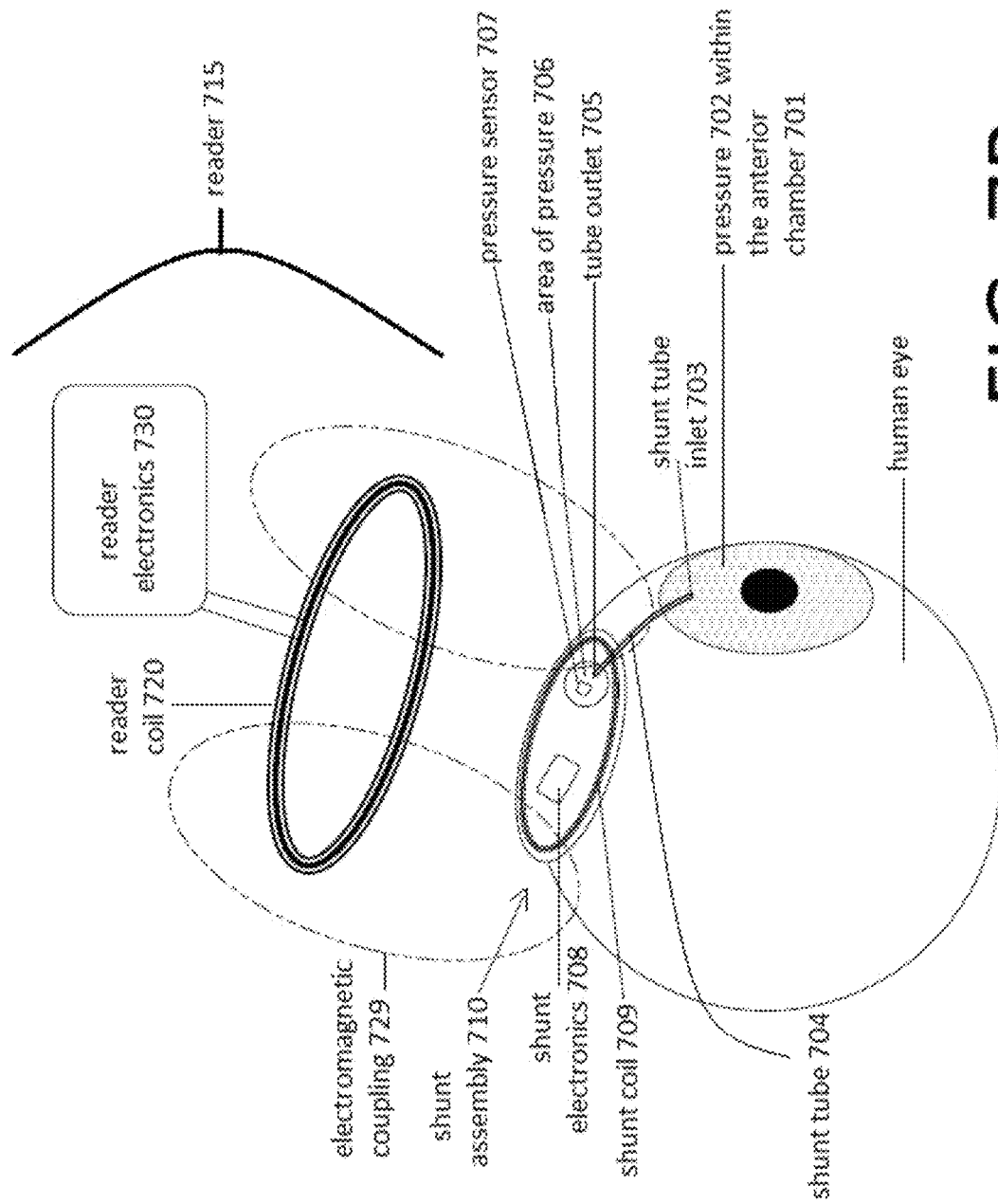
Figure 7D:
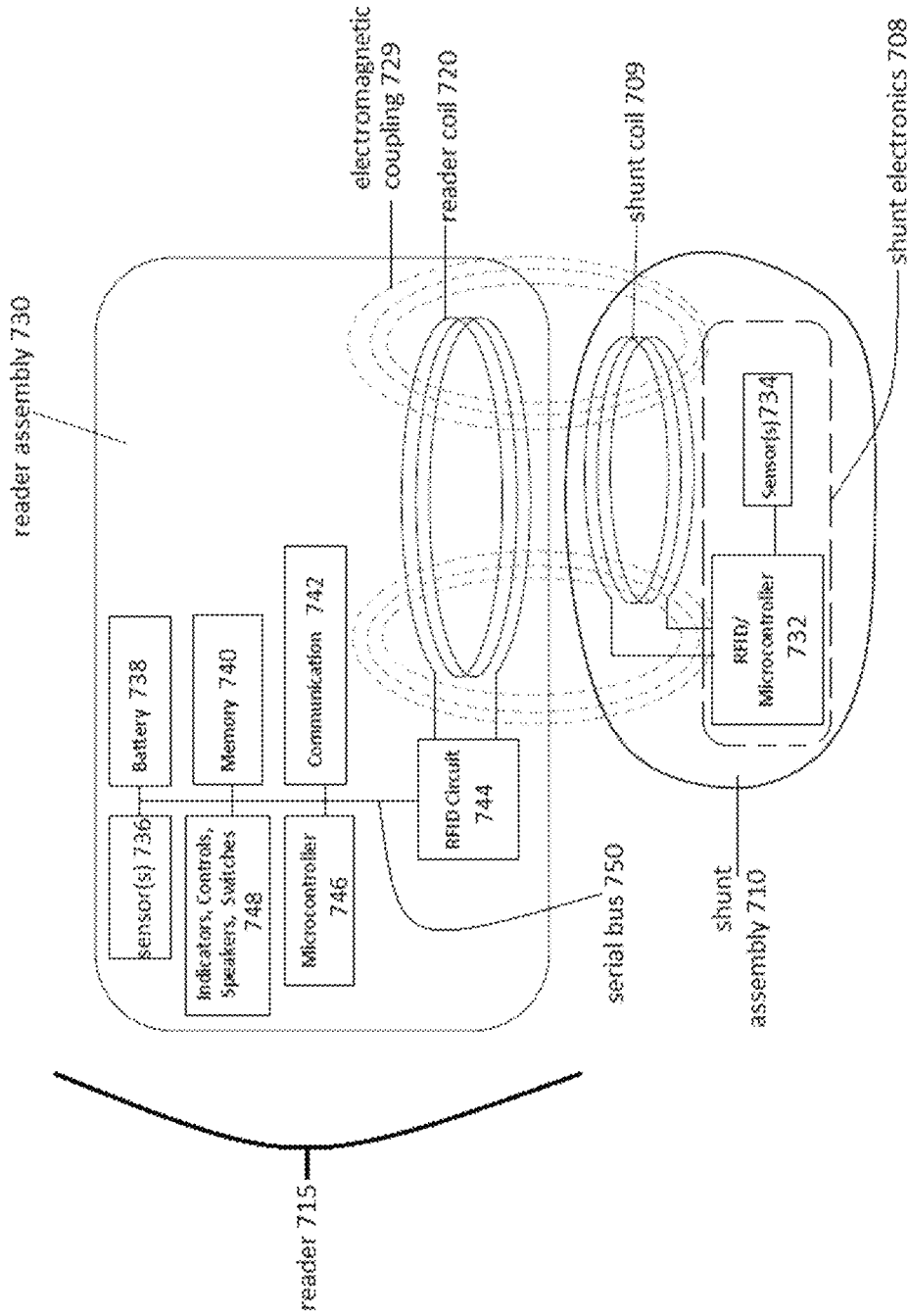

FIG. 7B then shows various of the elements of FIG. 7A as they are positioned with respect to a human eye. FIG. 7D shows details of the complex ter-relationships of the elements of FIGS. 7A-7B. Meanwhile, FIG. 7C shows a flowchart of method steps for operating the elements of FIGS. 7A, 7B, and 7D.

The reader 715 provides an alternating electromagnetic field to wirelessly supply energy to the shunt electronics 708 (see FIGS. 7A, 7D). The same electromagnetic field used to supply energy can also be used to provide a communications link between the reader 715 and shunt assembly 710 through the electronic coupling 729. The shunt electronics 708 receive the alternating field and then rectify, filter, and regulate to form a direct current source for operating logic and sensors shown in, for example, FIGS. 7B and 7D.

In an embodiment, a command is issued from the reader 715 to instruct the shunt electronics 708 to matte one or more sensor measurements. The shunt electronics 708 then operates the various of the sensors (e.g. sensors 734, 736 from FIG. 7D) to obtain e.g. pressure (IOP) and temperature measurements. This measurement data is then processed by the shunt electronics 708. The sensor data is then wirelessly conveyed to the reader 715 automatically, or when a command is issued from the reader 715. As shown in FIG. 7D, one embodiment of the system 700 uses a programmable microcontroller 746 or system logic and s functionality of the system 700 can be programmed.

Data processing performed by the system 700 can include, but is not limited to: averaging of sensor data to reduce noise and improve measurement quality, correction Or calibration of data. to improve accuracy, or calculations to determine when valid data has been measured. Data can also be processed in the reader 715. Barometer pressure corrections and calibration factors can be used to improve data accuracy. Identification data can be added to device communications to allow tracking of data using e.g. a device serial number, patient ID, or other relevant data.

As shown in FIG. 7D, the sensor(s) 736 communicates with the microcontroller 746 via a serial bus 750. Measurements are made by sending data from the microcontroller 746 to registers (memory locations) within the sensor(s) 736. The data in these registers acts as settings to configure the sensor(s) 736 for e.g. resolution, sample rate, and offset reference pressure and temperature. Pressure and temperature measurements are stored in registers and are read by the microcontroller 746.

FIG. 7C shows a method of operating the system 700. At step 780, the reader coil 720 is placed into proximity to the shunt coil 709, so that electromagnetic coupling 729 can occur. At step 784, a current generated into the reader coil 720 induces a voltage in the shunt coil 709. The voltage across the shunt coil 709 is applied to operating various sensor(s) 734 located within the shunt assembly 710. The data generated by those sensor(s) 734 is convey dot the reader coil 709 or, potentially, other wireless linked devices. At step 796, viewing, recording, and communication IOP as well as other relevant eye-data is now enabled.

This completes the description of FIGS. 7A-7D. The following remarks apply to all embodiments, where appropriate.

Although the electronic substrates used within the embodiments herein will likely contain flexible areas, these substrates may also have areas that are stiff that are caused by attached components like ICs or caused by added items to stiffen or protect the assembly. The example embodiments shown herein can work with either flexible shunt plate or a rigid shunt plate.

A typical conventional glaucoma shunt plate assembly is designed to conform the shape of the eye. Its placement is against the sclera and under the conjunctiva. As such, a portion or entirety of the substrate supporting the electronics e.g. 112\312\708, may thus be flexible, in order to facilitate conforming the electronics assembly to the shape of the shunt, plate and eye. The flexible substrate may also be stretchable to aid in shaping the substrate over a spherical shape. Serpentine or alternative patterns of conductors may be used to aid in shaping the substrate without breaking the conductors. The substrate may also include conductive patterns applied to the shell 104 or integrated within the shell 104.

The flexible substrates discussed herein may be fabricated using the conventional process of etching metal clad films, or may fabricated using processing more typically used for MicroElectroMechanical System (MEMS) processing where metal deposition, patterning, and plating is used. The MEMS fabrication has the advantage of higher resolution.

Areas of the electronic assemblies discussed herein may also be coated or covered with a material for the purpose of providing a smooth surface for tissue contact and to protect electronic components from physical harm. The electronic assembly may also be integrated entirely within the shell 104.

Moving to specific techniques of measurement, as discussed earlier, it is generally understood that a "gold standard" for IOP measurement is Goldman Applanation Tonometry (GAT). During a GAT measurement, the cornea is slightly flattened and the force required to do this correlates to intraocular pressure (IOP). Although GAT is considered the most accurate clinical measurement approach, GAT is still influenced by the thickness of the cornea. Furthermore, the GAT method requires a skilled operator and is less comfortable for the patient than other approaches.

To address these and other issues, the embodiments herein are directed to a direct pressure measurement technique. Pressure from within the eye operates directly on the various sensors and thus the corneal or sclera thickness does not impact the measurement. The sensors are thus functionally in-vivo. In this configuration, an IOP measurement is a process of simply wirelessly interrogating the various sensor(s) e.g. 116\736, where no preparation for the measurement is required and the measurements can be made by the patient at any time. No special skills are required.

In an embodiment, the pressure (IOP) measurements can be made on the proximal end of the shunt tubes (e.g. 120/704). If a GAT measurement differs from measurements obtained by the embodiments herein, this could suggest that the shunt tubes e.g. 120/704 are not operating as intended. A tube, or tube ends, can become occluded. To address this, the advantageous designs of the sensing mechanisms discussed herein provide a way to quickly detect and correct such a condition.

Turning to for example the pressure sensor 707 shown in e.g. FIG. 7B, a MicroElectroMechanical System (MEMS) pressure sensor used within the embodiments herein may contain a diaphragm that is sufficiently flexible to deflect due to fluid pressure. This deflection is sensed as strain using piezoresistors located within the diaphragm. The specific resistance-levels of the piezoresistors can be measured using an analog to digital converter circuit. The conversion process is managed by digital control from the microcontroller 746.

One difficulty is the tubes e.g. 120/704 are generally a separate piece from a plate or shell 104, that is, molded separately, and put together later. In an embodiment, the shunt tube e.g. 120/704 is included in the molding process for manufacturing the plate. Doing so overcomes or reduces the problem of clogging of ends of the shunt tube e.g. 120/704.

Specifically, the embodiments herein can be cast using two-step process. The shell e.g. 104 within the embodiments herein is not limited. That is, no need for the embodiments to be either all-flex, or all-rigid. In certain areas of a specific embodiment of the shell e.g. 104, being rigid can be an advantage. Meanwhile, in other areas of a specific embodiment, being flexible can be an advantage. Thus, a first step can be a flex-step, comprising e.g. molding or heat-treatment of a shell 104. Afterwards, a separate second step can be rigid-izing only certain selected portions of the shell 104.

In manufacturing the shell e.g. 104, low-temperature (under 120 C) molding is possible, as for example poly vinylmethyl siloxane (PVMS) cures at room-temperature. It is also possible to glue the two parts together, then "dip" them into a coating. It is also contemplated to mold (verb) one part, lay some electronics in, put a cover over the top, and then cast (verb) the rest of the components that were not in the original mold, thereby forming a completed system e.g. 100/300/700.

It is also contemplated to write conductive traces onto a 3-D object plate/shell 104, using a type of inkjet printing that prints conductors onto a hard shell, and then it is possible to coat over the top of these conductors. In such a case, any glaucoma device, including embodiments outside this disclosure, could be augmented by having various of the additional electronics discussed herein included therein, and then adding another coating layer.

Testing and Verification

To verify that the manufacturing processes described herein are working properly, prior to installation in a human eye there are ways to affirm that the systems e.g. 100\300\700 will work properly. It is desired to flush out and verify bugs, problems, or errors prior to installation in a human eye.

Specifically, it is possible to test pressure transfer through a system 100\300\700 using, for example, DI water. To achieve this prior-installation testing, a fast pressure response and pressure drop across the shunt tube 120\704 is measured. Specifically, pressure can be measured in the fluid reservoir near a distal end of the shunt tube 120\704. The pressure source is the anterior chamber 701 (e.g. FIG. 7A) where the proximal (not distal) end of the shunt tube 120\704 is placed. The pressure drop across the shunt tube 120\704 should be minimal and can be verified by monitoring. For example, a known pressure can be supplied to the proximal end of the shunt tube 120\704 while the distal end pressure is monitored. Pressure differences under 1 mmHg should be observed, which can be interpreted to mean that the system 100\300\700, especially the IOP sensors contained therein, are working properly and thus ready for installation.

It is possible to test the active circuit arrangement as follows, prior to surgical installation: reading the drainage device 102 with a reader unit e.g. reader 715. Atmospheric pressure will first be measured, meaning that no pressure is applied. This facilitates a baseline measurement. The systems 100\300\700 device can then be placed in a closed container capable of being configured to have variable pressure conditions which can be accurately relied upon, and then re-pressurized to obtain measurements at numerous variations above and below atmospheric pressure, where those variations emulate typical IOP variations of a typical glaucoma patient. The reader e.g. reader 715 can then be compared with the known pressure conditions imposed on the closed container.

There are numerous other ways to debug, test, verify, and install the systems 100\300\700 so as to be sure the system will be effective once it goes inside somebody's eye-socket. Testing the systems immediately after installation is limited because tissue has not fully conformed to cover the reservoir area of the shunt. The shunt tubes 120\704 can be read to verify some basic functions, but a tonometer versus shunt test is probably not yet meaningful, as it's too early in the process to have reliable data.

To address this, the embodiments disclosed herein can include special software to allow the systems 100\300\700 to be read without the patient interface. This would certainly be a convenient feature during installation.

Figure 8D:
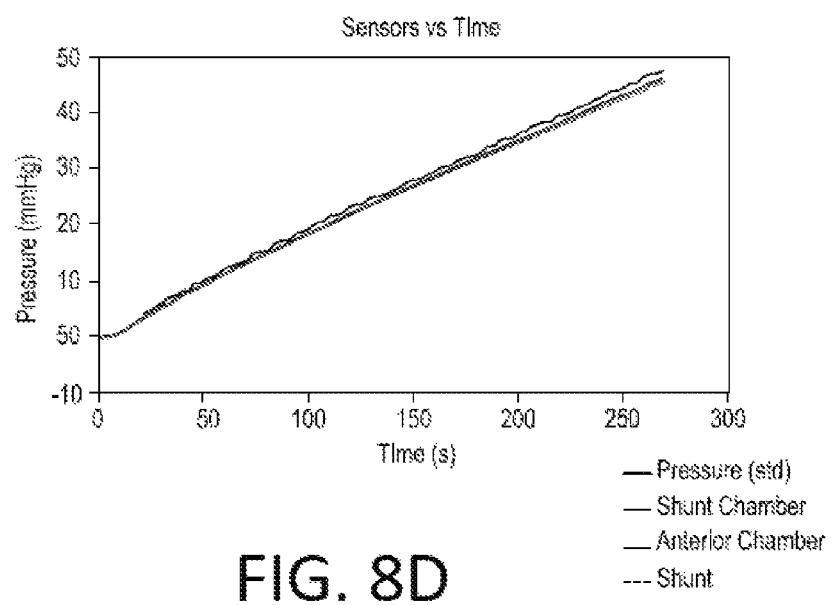
FIG. 8D shows a plot of sensors v. time.
Figure 8E:
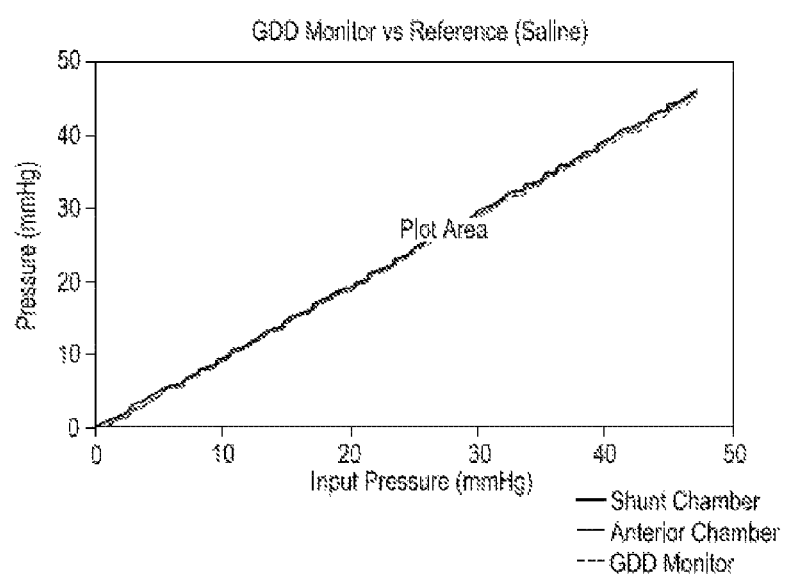
FIG. 8E shows a plot of the system v. a reference (saline).

FIGS. 8A, 8B, and 8C show data accumulated from running 88 separate pressure tests, over time. FIG. 8D shows a plot of sensors v. time. FIG. 8E shows a plot of the system v. a reference (saline). The plot includes shows the pressure in the benchtop model of the anterior chamber matching the pressure in the shunt chamber. The systems 100\300\700 match the shunt chamber pressure. The test demonstrates that is possible to accurately measure pressure in the anterior chamber by taking measurement at an opposite end of the shunt tubes 120\704. Additionally, FIGS. 8A-8E help demonstrate that the pressure measurement made by the systems 100\300\700 in the shunt chamber matches the pressure made by the reference sensor in the shunt chamber. As such, the tests documented herein confirm proper operation of the systems 100\300\700.

Manufacturing Steps

It is possible to implement the various systems 100\300\700 described herein using a single substrate. However, it can also be advantageous to having one substrate hold the electronics components where a separate substrate or wire antenna is added later. This is at least partly because the antenna portion of the systems 100/300/700 is highly flexible and shaped to conform to a human eye, while an area near the circuits and sensors may not be as flexible.

Regarding the flexible PCB, there can be a variety of ways by which the various chip-components are attached to thereto. One option is soldering, but other options are solder epoxy bonding, or thermal compression bonding. Either could use either using gold bumped or wire bonds.

Various types of coating, inert coatings, can allow the systems 100\300\700 to remain in-place and yet not react with the natural fluid of a person's eye. The coatings being considered are parylene C and PDMS (silicone polymer). In addition to these coatings, PMMA (acrylic) features could be added to protect the device or surround tissue. For example, a domed cap could be placed over a flat IC to prevent corners of the IC from damaging the coating and to create a smooth shape for tissue to rest against. Likewise, a layer of PDMS or PMMA buffer-like surface could be placed against the sclera (FIG. 2A) to reduce the chance of hard and soft eye-tissue areas that might form from having rigid components in the shunt body.

Another manufacturing and use consideration is that the flexible PCB must work well chemically with lubricant, or emulsion, and drops that are used by e.g. glaucoma patients. In such a case, the flexible PCB can be treated with a chemical process, e.g. coating, treating, during manufacture, that reduces irritation and sensitivity, and also does not cause any type of counter-reaction or unexpected by-product when coming in contact with e.g. glaucoma medications.

It is important that the flexible PCB of course achieve all the necessary mechanical features described herein (e.g. thin-ness, flexibility, etc) but also have the necessary chemical composition and reactive capability to properly maintain their mechanical and chemical during installation and use. This includes working well with the various anti-inflammatory or analgesic drugs and medications normally taken by a glaucoma patient who may not have a glaucoma system installed. Next, under certain medical conditions, various anti-inflammatory or analgesic drugs, which may differ from those alluded to earlier, can be administered to the tissue around the systems 100\300\700, to reduce inflammation and irritation for the wearer.

Further Embodiments

Electrodes could be added to the flexible circuit patterns already shown, or to an additional component. These electrodes would serve to detect the presence of, and potentially communicate with, a resource monitor near the electronic components.

What is claimed is:

1. A method of manufacturing a glaucoma inter ocular pressure (IOP) system, comprising:
configuring the system to have a shell comprising eyelets, a reservoir, and a drain tube;
integrating an arrangement of low-power electronics, at least one electronic sensors, and wireless telemetry to form a drainage device within the shell;
configuring the arrangement of low-power electronics to convert at least one outputs from the at least one sensors into a signal;
facilitating the arrangement such that the signal is wirelessly conveyed to a separate reader through the wireless telemetry; and
locating the reader in close proximity to the drainage device during eventual use.

2. The method of claim 1, further comprising:
configuring the shell to have a plurality of contours that conform with typical contours of a human eye.

3. The method of claim 2, further comprising:
embedding the at least one electronic sensors, wireless telemetry, and arrangement of low-power electronics within a flexible printed circuit board.

4. The method of claim 3, further comprising:
architecting the flexible printed circuit board to exactly conform with a plurality of contours within the shell.

5. The method of claim 3, further comprising:
the flexible printed circuit board adhering to greater than 80% of a surface area of the shell.

6. The method of claim 3, further comprising:
the flexible printed circuit board having system eyelets which match with and adhere to the eyelets of the shell.

7. The method of claim 3, further comprising:
the reader providing power to the flexible printed circuit board.

8. The method of claim 3, further comprising:
a super capacitor providing power to the flexible printed circuit board.

9. The method of claim 3, further comprising:
forming the flexible printed circuit board to also be stretchable, thereby aiding in shaping a substrate over at least one contours of the shell; and
incorporating alternative patterns of conductors to assist in shaping the substrate without breaking the conductors.

10. The method of claim 3, further comprising:
forming a domed cap over the flexible printed circuit board, thereby preventing corners of the circuit board from damaging a coating and to create a smooth shape for eye-tissue to rest against;
locating a buffer layer of silicone polymer (PDMS) or polymethyl acrylate (PMMA) to adjoin against a sclera, thereby reducing forming of hard and soft eye-tissue areas due to potential contact with components within the flexible printed circuit board.

11. The method of claim 1, further comprising:
molding the shell using low-temperature under 120° C. polyvinyl methyl siloxane (PVMS) which cures at room-temperature.

12. The method of claim 1, further comprising:
manufacturing the shell using two-step process, comprising;
molding a first portion of the shell;
molding a second portion of the shell;
gluing the two portions together; and
dipping the two portions into a coating.

13. The method of claim 1, further comprising:
implementing the system described herein using a single conductive substrate.

14. The method of claim 1, further comprising:
implementing a first substrate holding the various electronics components; and
afterwards, after testing and verification, adding a separate substrate.

15. The method of claim 1, further comprising:
embedding the at least one electronic sensors, wireless telemetry, arrangement of low-power electronics, and flexible printed circuit board within a pre-existing pre-purchased pre-tested glaucoma IOP system.

16. The method of claim 1, further comprising:
forming the shell, then
writing conductive traces onto the shell; then
inkjet printing a plurality of conductors onto the shell; and
coating over the top of the plurality of conductors.

* * * * *